US011416653B2

(12) United States Patent
Downs et al.

(10) Patent No.: US 11,416,653 B2
(45) Date of Patent: Aug. 16, 2022

(54) NUMERICAL MODEL OF THE HUMAN HEAD

(71) Applicant: The MITRE Corporation, McLean, VA (US)

(72) Inventors: Matthew E. Downs, McLean, VA (US); Joseph Dagher, McLean, VA (US)

(73) Assignee: The MITRE Corporation, McLean, VA (US)

( * ) Notice: Subject to any disclaimer, the term of this patent is extended or adjusted under 35 U.S.C. 154(b) by 358 days.

(21) Appl. No.: 16/412,709

(22) Filed: May 15, 2019

(65) Prior Publication Data

US 2020/0364312 A1 Nov. 19, 2020

(51) Int. Cl.
*G06F 30/20* (2020.01)
*G06F 17/18* (2006.01)
(Continued)

(52) U.S. Cl.
CPC ......... *G06F 30/20* (2020.01); *G01R 33/0064* (2013.01); *G01R 33/56* (2013.01);
(Continued)

(58) Field of Classification Search
CPC ..... G06N 20/00; G06F 2111/10; G06F 17/18; G01R 33/0064; G01R 33/56; G01R 33/58
(Continued)

(56) References Cited

U.S. PATENT DOCUMENTS

| 7,072,705 | B2 * | 7/2006 | Miga | G06V 20/653 |
| | | | | 600/411 |
| 8,781,197 | B2 * | 7/2014 | Wang | G01R 33/54 |
| | | | | 382/131 |

(Continued)

FOREIGN PATENT DOCUMENTS

| DE | 102004006561 | 8/2005 |
| DE | 202012011452 | 4/2013 |

OTHER PUBLICATIONS

Baumgartner et al. (Numerical Modeling of the Human Head Under Impact: New Injury Mechanisms and Tolerance Limits, 2005, Springer, pp. 195-203) (Year: 2005).*

(Continued)

*Primary Examiner* — Iftekhar A Khan
(74) *Attorney, Agent, or Firm* — Morrison & Foerster LLP (57) ABSTRACT

Systems and methods for generating a numerical model of the human head are provided. A numerical model may be created by generating a data array in a magnetic resonance modeling system, each cell of the array corresponding to a location in the head. The cells may be grouped into one or more regions, each group corresponding to a segment of the head. The cells of the array may be populated with values corresponding to tissue properties relevant to MR imaging. Tissue property values may be selected for each region based on one or more probability distributions. For each region and each tissue property, a value may be selected based on a corresponding probability distribution. Selected tissue property values may be input into cells in the array corresponding to the region with which the probability distribution is associated. The numerical model may be used as an input to an MRI simulator.

18 Claims, 7 Drawing Sheets

(51) Int. Cl.
G01R 33/00 (2006.01)
G01R 33/58 (2006.01)
G06N 20/00 (2019.01)
G01R 33/56 (2006.01)
G06F 111/10 (2020.01)

(52) U.S. Cl.
CPC ............. *G01R 33/58* (2013.01); *G06F 17/18* (2013.01); *G06N 20/00* (2019.01); *G06F 2111/10* (2020.01)

(58) Field of Classification Search
USPC .......................................................... 703/2
See application file for complete search history.

(56) References Cited

U.S. PATENT DOCUMENTS

| | | | | |
|---|---|---|---|---|
| 10,957,442 | B2* | 3/2021 | Kalafut | G16H 50/20 |
| 11,042,982 | B2* | 6/2021 | Liu | A61B 5/316 |
| 2002/0184470 | A1* | 12/2002 | Weese | G06T 7/149 |
| | | | | 712/1 |
| 2003/0006770 | A1* | 1/2003 | Smith | F23C 9/00 |
| | | | | 324/309 |
| 2005/0148852 | A1* | 7/2005 | Tank | A61B 8/00 |
| | | | | 600/407 |
| 2009/0226060 | A1* | 9/2009 | Gering | G06T 7/174 |
| | | | | 382/128 |
| 2009/0292198 | A1* | 11/2009 | Kleiven | G16Z 99/00 |
| | | | | 600/416 |
| 2011/0229005 | A1* | 9/2011 | Den Harder | G06T 7/11 |
| | | | | 382/128 |
| 2011/0254548 | A1* | 10/2011 | Setsompop | G01R 33/543 |
| | | | | 324/309 |
| 2012/0043964 | A1* | 2/2012 | Schreck | G01R 33/58 |
| | | | | 324/309 |
| 2013/0116540 | A1* | 5/2013 | Li | A61B 5/7246 |
| | | | | 600/410 |
| 2013/0338930 | A1* | 12/2013 | Senegas | G01R 33/546 |
| | | | | 702/19 |
| 2014/0148657 | A1* | 5/2014 | Hendler | A61B 8/0808 |
| | | | | 600/545 |
| 2015/0146951 | A1* | 5/2015 | Zagorchev | G06T 7/149 |
| | | | | 382/131 |
| 2015/0212177 | A1* | 7/2015 | Ahmad | G01R 33/5619 |
| | | | | 324/309 |
| 2015/0212182 | A1* | 7/2015 | Nielsen | G01R 33/56509 |
| | | | | 702/191 |
| 2016/0327606 | A1* | 11/2016 | Van Wieringen | G06N 3/0472 |
| 2016/0338613 | A1* | 11/2016 | Beckers | A61B 5/0263 |
| 2017/0038452 | A1* | 2/2017 | Trzasko | G01R 33/482 |
| 2018/0137941 | A1* | 5/2018 | Chen | G06N 3/04 |
| 2018/0203081 | A1* | 7/2018 | Cohen | G06N 3/08 |
| 2018/0276822 | A1* | 9/2018 | Liu | A61B 5/374 |
| 2018/0310854 | A1* | 11/2018 | Geva | A61B 5/7239 |
| 2018/0321347 | A1* | 11/2018 | Wang | G01R 33/5608 |
| 2019/0056470 | A1* | 2/2019 | Wang | A61B 5/055 |
| 2019/0057623 | A1* | 2/2019 | Magsood | G01R 33/58 |
| 2019/0180145 | A1* | 6/2019 | Chen | G16Z 99/00 |
| 2019/0353732 | A1* | 11/2019 | McGivney | G01R 33/5608 |
| 2020/0011953 | A1* | 1/2020 | Tomi-Tricot | G01R 33/5613 |
| 2020/0034998 | A1* | 1/2020 | Schlemper | A61B 5/055 |
| 2020/0065969 | A1* | 2/2020 | Huang | G06T 7/0012 |
| 2020/0072931 | A1* | 3/2020 | Zaiss | G06N 20/10 |
| 2020/0118691 | A1* | 4/2020 | Kiljanek | G06N 20/00 |
| 2020/0209335 | A1* | 7/2020 | O'Halloran | G01R 33/389 |
| 2020/0211692 | A1* | 7/2020 | Kalafut | G06N 20/00 |
| 2020/0226827 | A1* | 7/2020 | Kim | G06N 20/00 |
| 2020/0249301 | A1* | 8/2020 | Polak | G16H 30/20 |
| 2020/0364312 | A1* | 11/2020 | Downs | G06F 17/18 |
| 2021/0041518 | A1* | 2/2021 | Okuda | G01R 33/4822 |

OTHER PUBLICATIONS

Makris et al. (MRI-based anatomical model of the human head for specific absorption rate mapping, Med Biol Eng Comput. 2008, pp. 1239-1251) (Year: 2008).*

Ropella et al. (A Regularized, Model-Based Approach to Phase-Based Conductivity Mapping Using MRI, 2017, Magnetic Resonance in Medicine, pp. 2011-2021) (Year: 2017).*

Esteban et al. (Feb. 2016). "Diffantom: Whole-brain Diffusion MRI Phantoms Derived From Real Datasets of the Human Connectome Project," Frontiers in Neuroinformatics 10(4): 7 pages.

Perrone et al. (Mar. 2016) "D-BRAIN: Anatomically Accurate Simulated Diffusion MRI Brain Data," PLoS ONE 11(3): 23 pages.

Protti et al. (Jul. 2018) "Development and Validation of a New MRI Simulation Technique That Can Reliably Estimate Optimal In Vivo Scanning Parameters in a Glioblastoma Murine Model," PLoS ONE 13(7): 22 pages.

* cited by examiner

NUMERICAL MODEL OF THE HUMAN HEAD

FIELD OF THE INVENTION

This invention relates to systems, methods, and user interfaces for simulating MRI measurements of the human head. In particular, the systems and methods allow users to generate a numerical model of the human head that may be used to generate synthetic magnetic resonance images of the human head.

BACKGROUND OF THE INVENTION

To be reliable, MRI measurement methods must be validated based on information known by direct observation to be true, or a "ground truth." An MRI measurement method may be validated against a ground truth in multiple ways. For example, an MRI measurement method may be validated by comparing an MRI image directly to a biopsy of the imaged tissue. This is often an invasive operation and requires access to tissue. Alternatively, an MRI measurement method may be validated by imaging a physical synthetic object with known properties—a "phantom"—and comparing the MRI image to the known properties of the phantom. Finally, an MRI measurement method may be validated by using a software-defined MRI simulator to generate an image based on a computer model of the tissue with known properties—a "numerical phantom" or "numerical model"—and comparing the image to the known properties of the model. Currently, no numerical model of the human head exists that models tissue properties based on ground truth data.

SUMMARY OF THE INVENTION

As discussed above, there is a need for a synthetic way to accurately model tissue properties of a human head in software. This need may be addressed by the methods disclosed herein for configuring and generating a numerical model of a human head. In one or more embodiments, the method allows a user to generate a data array in a magnetic resonance modeling system corresponding to a model of a human head, with each cell of the array corresponding to a location in the head. Each cell in the data array may correspond to a location in the head comprising brain tissue, bone tissue, cerebrospinal fluid, sinuses, soft tissue, eyes, or other material. The cells may be grouped into one or more regions, each group corresponding to a segment of the head. The size of one or more regions may be modified to generate a model of a head having a unique structure. Additionally, one or more regions corresponding to one or more neuropathologies, such as tumors or cerebral microbleeds, may be added to the model.

The cells of the data array may be populated with values corresponding to tissue properties relevant to MR imaging, such as T1, T2, T2*, iron concentration, water fraction, or other properties. Tissue property values may be selected for each region based on one or more probability distributions, or based on a user specified input. A probability distribution may correspond to one tissue property and one region of the head. A tissue property probability distribution may include one or more tissue property values and a probability associated with each value. A probability distribution may be based on samples of tissue property measurements of the region of the head to which the distribution corresponds. For each region and each tissue property, a value may be selected based on a corresponding probability distribution. Selected tissue property values may be input into cells in the array corresponding to the region with which the probability distribution is associated.

The generated model may be used as an input to an MRI simulator, and MR images may be generated based on the model. The generated model may also be used as an input to post-processing and analyses software.

In some embodiments, a method for generating a numerical model of the head is provided, comprising: generating an array in a memory of a magnetic resonance modeling system, each cell in the array corresponding to a location in the head, wherein generating the array comprises: grouping cells of the array that correspond to different segments of the head, and populating the grouped cells of the array to generate a numerical model of using one or more probability distributions of tissue property values of a head, wherein the probability distributions comprise tissue property values associated with locations in the head and corresponding probability values, and wherein populating the grouped cells comprises: for each group of cells, determining a tissue property value based on one or more probability distributions associated with the segment of the head to which the group of cells corresponds.

In some embodiments, the method comprises inputting the numerical model into an MRI simulator to generate a simulated magnetic resonance image based on a simulated pulse sequence.

In some embodiments, the method comprises reconstructing an estimate of the tissue property values selected from the one or more probability distributions.

In some embodiments, the method comprises comparing the reconstructed estimate of the tissue property values to the tissue property values on which the numerical model is based.

In some embodiments, the method comprises adjusting the simulated MRI pulse sequence based on differences between the reconstructed estimate of the tissue property values and the tissue property values on which the numerical model is based.

In some embodiments, the method comprises comparing the simulated magnetic resonance image with an output of a clinical MRI machine and calibrating the clinical MRI machine based on differences between the simulated magnetic resonance image and the output of the clinical MRI machine.

In some embodiments of the method, the probability distributions comprise Gaussian distributions based on one or more measurements of tissue property values.

In some embodiments of the method, populating the grouped cells of the array using one or more probability distributions of tissue property values of a head comprises selecting, for each group of cells, a probability distribution corresponding to one tissue property.

In some embodiments of the method, at least one group of cells corresponds to a neuropathology.

In some embodiments of the method, populating the grouped cells of the array further comprises selecting a probability distribution from a plurality of libraries of probability distributions, each library of probability distributions comprising tissue property values derived from different measurements.

In some embodiments of the method, the probability distributions comprise tissue property values corresponding to a tissue property selected from the group consisting of electromagnetic susceptibility, iron concentration, real oximetry, tissue molecular composition, T1, T2, or T2*.

In some embodiments of the method, the magnetic resonance modeling system is an MRI simulator.

In some embodiments of the method, the cells composing the one or more groups of cells are adjacent.

In some embodiments, the method comprises adjusting the boundary of at least one of the one or more groups of cells by adding or removing at least one cell.

In some embodiments, an electronic system is provided, comprising: one or more processors, one or more memories, and one or more programs, wherein the one or more programs are stored in the one or more memories and configured to be executed by the one or more processors, the one or more programs including instructions for generating an array in a memory of a magnetic resonance modeling system, each cell in the array corresponding to a location in the head, wherein generating the array comprises: grouping cells of the array that correspond to different segments of the head, and populating the grouped cells of the array to generate a numerical model of using one or more probability distributions of tissue property values of the head, wherein the probability distributions comprise tissue property values associated with locations in the head and corresponding probability values, and wherein populating the grouped cells comprises: for each group of cells, determining a tissue property value based on one or more probability distributions associated with the segment of the head to which the group of cells corresponds.

In some embodiments, a non-transitory computer-readable storage medium storing instructions for generating a numerical model of the human head is provided, the instructions configured to be executed by one or more processors of a system comprising a display, and one or more processors, the instructions configured to cause the system to generate an array in a memory of a magnetic resonance modeling system, each cell in the array corresponding to a location in the head, wherein generating the array comprises: grouping cells of the array that correspond to different segments of the head, and populating the grouped cells of the array to generate a numerical model of using one or more probability distributions of tissue property values of the head, wherein the probability distributions comprise tissue property values associated with locations in the head and corresponding probability values, and wherein populating the grouped cells comprises: for each group of cells, determining a tissue property value based on one or more probability distributions associated with the segment of the head to which the group of cells corresponds.

In some embodiments, a method of training a machine learning classifier to analyze MRI scans is provided, the method comprising: generating one or more normal numerical models of the human head, generating a plurality of abnormal numerical models of the human head, wherein each numerical model of the plurality of abnormal numerical models comprises one or more pathological features indicative of disease, generating simulated magnetic resonance images based on the one or more normal numerical models and the plurality of abnormal numerical models, and training a machine learning classifier to detect pathologies based on the simulated magnetic resonance images.

In some embodiments, a method of validating MRI pulse sequences is provided, the method comprising: generating a numerical model of the human head based on known tissue property values, defining a first MRI pulse sequence, simulating an MRI scan of the numerical model based on the first MRI pulse sequence, reconstructing an estimate of the tissue property values based on the result of the simulated MRI scan, comparing the reconstructed estimate of the tissue property values to the tissue property values on which the numerical model is based, and defining a second MRI pulse sequence based on differences between the reconstructed estimate of the tissue property values to the tissue property values on which the numerical model is based.

DETAILED DESCRIPTION OF THE INVENTION

Different measurement methods used during an MRI scan can generate different results. MRI measurement methods may be varied by changing, for example, the pulse sequence and/or post-processing used during a scan. For example, the pulse sequence used during an MRI scan can be varied to generate different image contrast between tissues. Post-processing techniques following a pulse sequence can also be varied tissue property estimates based on the same MRI data. An MRI measurement method may be useful for detecting and measuring some tissue properties, but not others.

As discussed above, to determine whether an MRI measurement method is accurate in detecting or estimating a particular tissue property, it must be validated based on information known by direct observation to be true. An MRI method may be validated in multiple ways. For example, an MRI measurement method may be validated by comparing an image generated by the technique directly to the imaged tissue. Alternatively, an MRI measurement method may be validated by imaging a physical synthetic object with known properties—a "phantom"—and comparing the generated image to the known properties of the phantom. Finally, an MRI measurement method may be validated by using a software-defined MRI simulator to generate an image based on a computer model of the tissue having known tissue properties—a "numerical model"—and comparing the generated image to the known properties of the model.

Numerical models have certain advantages over physical phantoms. For example, because numerical models are generated and stored as data, they are more portable than a physical phantom, may be more easily transmitted between researchers and facilities, and may be more easily modified and/or customized than a physical phantom. However, currently there are no available MRI simulators that utilize high resolution numerical models of the human head that incorporate tissue properties for certain neuropathologies and for all regions of the head. Thus, in order to develop and validate MRI measurement methods for measuring tissue properties of the human head, there exists a need for a numerical model of the human head.

Described herein are methods for configuring and generating a digital model of the human head that can be used with software defined MRI simulators. Different segments of the head have different tissue property values. The digital model of the head may accurately model one or more tissue property values for one or more locations in the head. The digital model may be used as an input to software defined MRI simulator, which may operate on the model to produce a simulated magnetic resonance image.

In one or more embodiments, the systems and methods described herein allow a user to generate a data array in a magnetic resonance modeling system corresponding to a model of a human head, with each cell of the array corresponding to a location in the head. Each cell in the data array may correspond to a location in the head comprising brain tissue, bone tissue, cerebrospinal fluid, sinuses, soft tissue, eyes, or other material. The cells may be grouped into one or more regions, each group corresponding to a segment of the head. The size of one or more regions may be modified to generate a model of a head having a unique structure. Additionally, one or more regions corresponding to one or more neuropatholigies, such as tumors or cerebral microbleeds, may be added to the model.

The cells of the data array may be populated with values corresponding to tissue properties relevant to MR imaging, such as T1, T2, T2*, iron concentration, water fraction, or other properties. Tissue property values may be selected for each region based on one or more probability distributions. A probability distribution may correspond to one tissue property and one region of the head. A tissue property probability distribution may include one or more tissue property values and a probability associated with each value. By selecting tissue property values based on probability distributions, unique numerical models may be generated having unique tissue properties.

A probability distribution may be based on sample of tissue property measurements of the region of the head to which the distribution corresponds. For each region and each tissue property, a value may be selected based on a corresponding probability distribution. Selected tissue property values may be input into cells in the array corresponding to the region with which the probability distribution is associated.

The generated model may be used as an input to an MRI simulator, and MR images may be generated based on the model.

Figure 1:
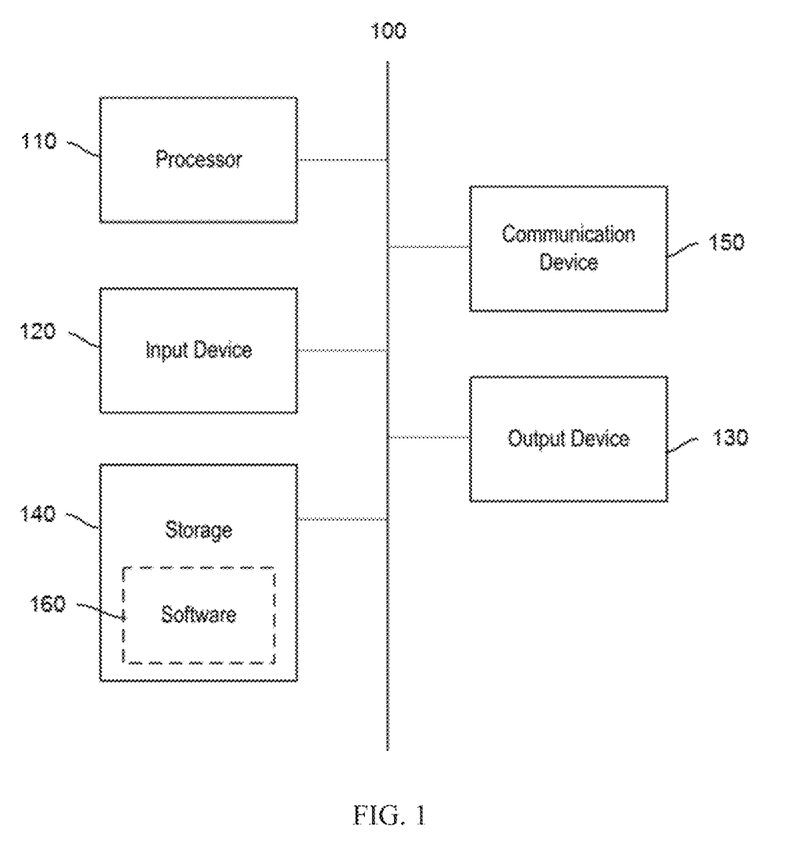
FIG. 1 is a functional block diagram of a magnetic resonance modeling system, according to some embodiments.

FIG. 1 illustrates an example of a magnetic resonance modeling system 100, in accordance with one embodiment. In some embodiments, system 100 is configured to execute a method for generating a numerical model of the human head, such as described with respect to method 200 of FIG. 2, below.

In some embodiments, system 100 can be any suitable type of microprocessor-based device, such as a personal computer, workstation, server, videogame console, or handheld computing device, such as a phone or tablet. The system can include, for example, one or more of processor 110, input device 120, output device 130, storage 140, and communication device 150. Input device 120 and output device 130 can generally correspond to those described above and can either be connectable or integrated with the computer.

In some embodiments, system 100 can be a computer. System 100 can be a local computer or a cloud computing platform. System 100 can include multiple computers. System 100 can be a host computer connected to a network. In other embodiments, system 100 can be a client computer or a server.

Input device 120 can be any suitable device that provides input, such as a touch screen or monitor, keyboard, mouse, or voice-recognition device. Output device 130 can be any suitable device that provides output, such as a touch screen, monitor, printer, disk drive, or speaker.

Storage 140 can be any suitable device that provides storage, such as an electrical, magnetic, or optical memory, including a RAM, cache, hard drive, CD-ROM drive, tape drive, or removable storage disk.

Communication device 150 can include any suitable device capable of transmitting and receiving signals over a network, such as a network interface chip or card. The components of the computer can be connected in any suitable manner, such as via a physical bus or wirelessly.

Figure 2:
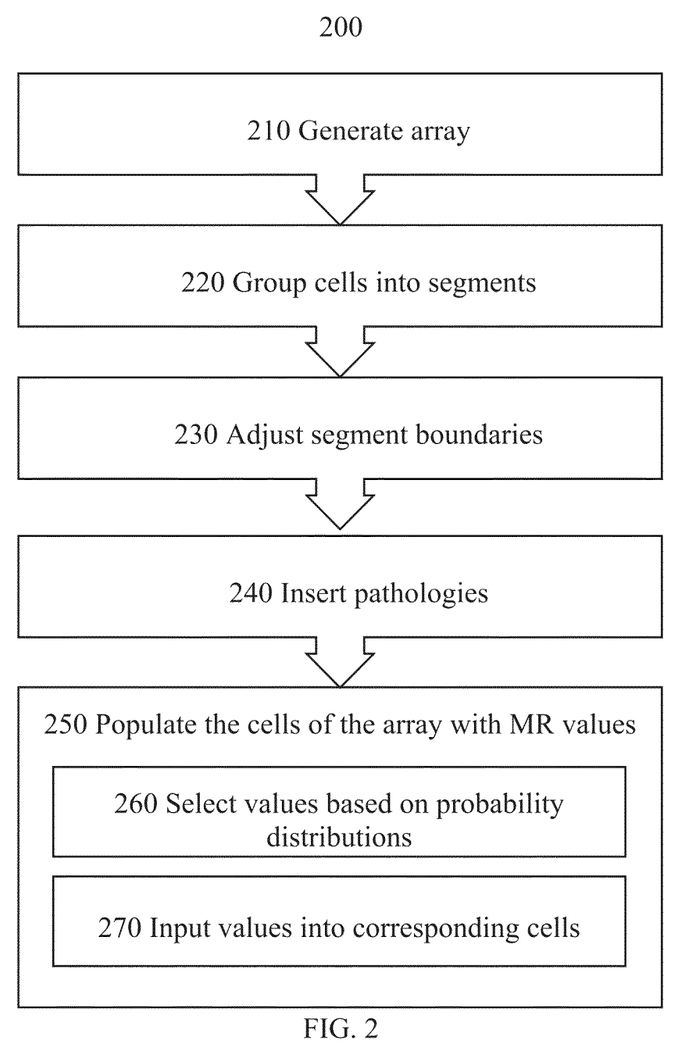
FIG. 2 is a flow diagram that illustrates a process for generating a numerical model of a human head, according to some embodiments.

Storage 140 can be a non-transitory computer-readable storage medium comprising one or more programs, which, when executed by one or more processors, such as processor 110, cause the one or more processors to execute methods described herein, such as method 200 of FIG. 2.

Software 160, which can be stored in storage 140 and executed by processor 110, can include, for example, the programming that embodies the functionality of the present disclosure (e.g., as embodied in the systems, computers, servers, and/or devices as described above). In some embodiments, software 160 can be implemented and executed on a combination of servers such as application servers and database servers.

Software 160, or part thereof, can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 140, that can contain or store programming for use by or in connection with an instruction execution system, apparatus, or device.

Software 160 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include, but is not limited to, an electronic, magnetic, optical, electromagnetic, or infrared wired or wireless propagation medium.

System 100 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

System 100 can implement any operating system suitable for operating on the network. Software 160 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

FIG. 2 illustrates a method 200 for generating a numerical model of the human head, according to some embodiments. Method 100 may be performed at a magnetic resonance modeling system, such as described above with reference to FIG. 1. In some embodiments, method 200 may enable a user to configure one or more aspects of a numerical model, such as the tissue properties incorporated in the model, and generate a numerical model in accordance with the user's preferences.

At step 210, a data array may be generated. The data array may comprise one or more cells, each cell corresponding to a location in the head. The data array may comprise a data object, such as a table, an array, a list, a tree, a linked list, or any other data structure suitable for storing related data values. The data array may be stored in memory, such as storage 140 described with respect to FIG. 1, above. Each cell in the data array may be a data object, such as a cell in a data array, a node in a linked list, or other suitable data structure.

The data array created and/or stored in memory may correspond to a two- or three-dimensional model of a head, with each cell of the array corresponding to a pixel or voxel of a two- or three-dimensional image of the head. The volume or region of the head to which each cell corresponds may comprise brain tissue, bone tissue, cerebrospinal fluid, sinuses, soft tissue, eyes, or other material.

In some embodiments, the data array created and/or stored in memory may correspond to a three-dimensional model of a head. In this case, the data array may be configured as a three-dimensional data array, wherein which each cell in the array is associated with a voxel of a three-dimensional image of the head, according to its position in the data array.

Alternatively, the data array created and/or stored in memory may correspond to a two-dimensional model of a two-dimensional "slice" of a head. In this case, the data array may be configured as a two-dimensional array, wherein each cell in the array is associated with pixel of a two-dimensional image of the head, according to its position in the array.

In other embodiments, the cells in the data array created and/or stored in memory may not be associated with a corresponding volume or region of the head based on a relationship between the region of the head to which the cell corresponds and the geometry of the array. Instead, the data array may comprise a plurality of cells, wherein each cell is associated with additional location values indicating to which volume or region of the head the cell corresponds. Location values may be generated and stored in memory, such as storage 140 described with respect to FIG. 1, above. A location value may be stored in the cell to which it corresponds, stored in a cell or data structure adjacent to the cell to which it corresponds, or stored in a location separate from the cell to which it corresponds.

The data array created and/or stored in memory may be of any size. That is, the data array may comprise any number of cells, data structures, and/or tissue property values. For example, the data array may comprise 134,217,728 cells or data structures, corresponding to a 512×512×512 model of the head. In some embodiments, the size of the data array may be selected to correspond to an image generated by a clinical MRI scan, such as an image having resolution of 512×512×512. That is, the number of cells in the array may be selected to correspond to a resolution of a clinical MRI scan and/or the output of a software-defined MRI simulator. Alternatively, the size of the data array may be selected by a user or selected in accordance with a default value. In other embodiments, the size of the data array may be selected to correspond to input requirements of MRI simulation software or other medical imaging software.

A cell may correspond to regions of the head of any size. For example, a cell may correspond to a 0.5 $mm^3$ volume of the head. In some embodiments, the size of a region to which a cell corresponds may be less than 0.25 $mm^3$, less than 0.5 $mm^3$, less than 1 $mm^3$, less than 5 $mm^3$, or less than 10 $mm^3$. In other embodiments, the size of a region to which a cell corresponds may be greater than 0.25 $mm^3$, greater than 0.5 $mm^3$, greater than 1 $mm^3$, greater than 5 $mm^3$, or greater than 10 $mm^3$. In some embodiments, the size of the region of the head to which a cell corresponds may be determined based on the number of cells in the model or may be based on the resolution of a clinical or simulated MRI scan.

Figure 3:
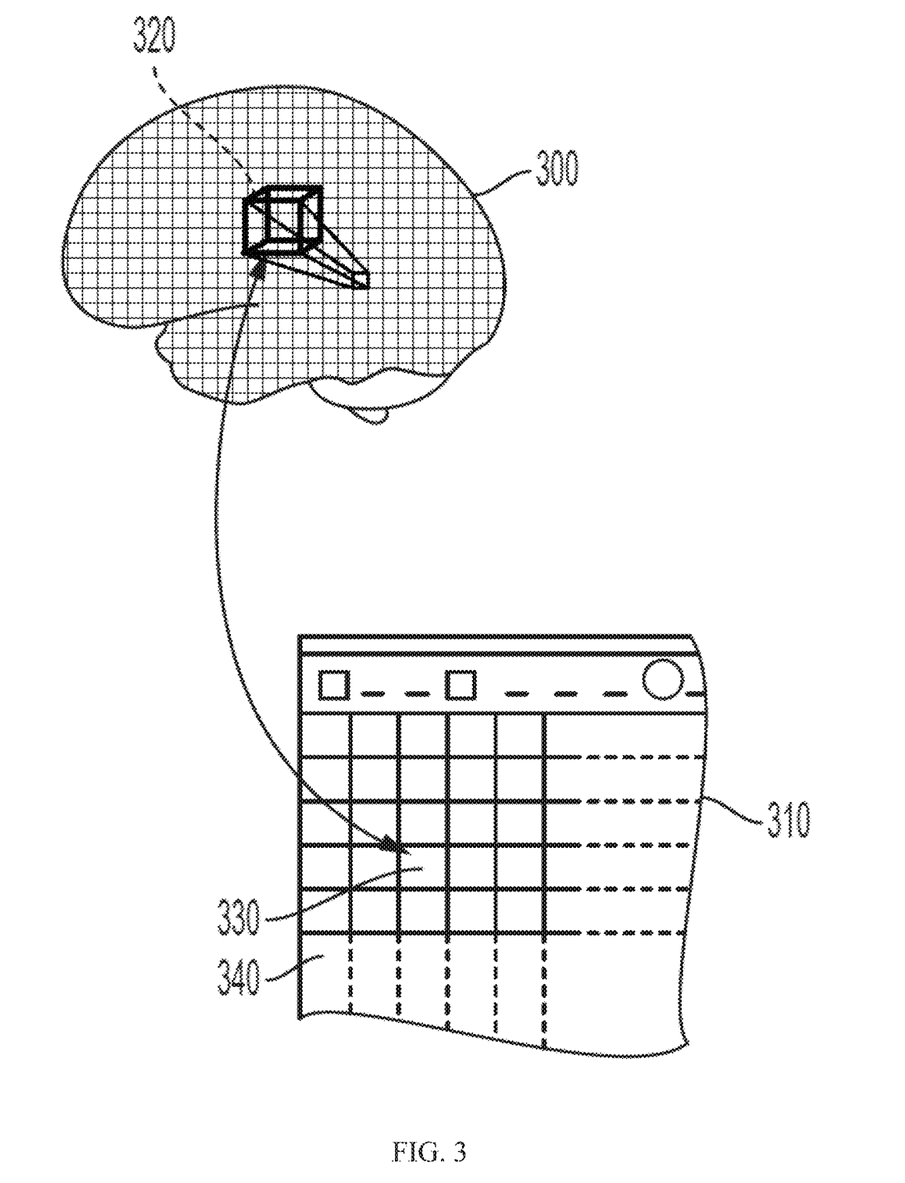
FIG. 3 is a depiction of a brain and corresponding data array, according to some embodiments.

FIG. 3 shows an exemplary depiction of a brain and a corresponding array, according to some embodiments. In other embodiments, the array may correspond to all regions of the head, including regions other than the brain. FIG. 3 includes a brain 300 divided into a plurality of three-dimensional regions, such as region 320, and a data array 310 comprising a plurality of cells, such as cell 330. In the example of FIG. 3, region 320 is associated with cell 310. Thus, cell 310 may store one or more tissue property values associated with region 320 of brain 300.

The association between region 320 and cell 330 may be defined and stored in a variety of ways. For example, cell 330 may also store data identifying region 320 as the brain region to which cell 330 corresponds. Alternatively, an adjacent data structure, such as column 340, may store data identifying the brain region to which adjacent cells correspond. In still further embodiments, information identifying the brain region to which cells in array 310 correspond may be stored in a data array, data file, or other data structure separate from array 310. In this way, a single array, data file, or data structure may function as a template that identifies the brain regions to which cells correspond for multiple data arrays that contain only tissue property values.

In some embodiments, the data array created and/or stored in memory may initially be empty when it is created. Alternatively, each cell in the data array may be populated with a single default value to indicate that the array has not yet been populated with tissue property values. In other embodiments, the data array may be populated with default tissue property values corresponding to one or more default tissue properties. Additionally, each cell in the data array may be associated with one or more coordinate values that correspond to the position of the cell within the array and/or identify the region of the brain to which the cell corresponds.

Returning to the method of FIG. 2, at step 220, the cells of the data array may be associated into one or more groups of cells—or "segments"—each group of cells corresponding to a region of the head, and each group comprising one or more cells. For example, the cells of the data array may be grouped into segments corresponding to regions of the head and/or regions of the brain, such as the skull, eyes, sinuses, amygdala, hippocampus, cerebellum, and/or any other region of the head. The data array may also be segmented into groups of cells based on the type of material associated with the corresponding region of the head. For example, the cells of the array may be grouped into segments corresponding to brain tissue, bone tissue, soft tissue, muscle, cerebrospinal fluid, white matter, and/or other materials. In some embodiments, grouped cells may correspond to adjacent locations in the head.

The data array may be grouped into any number of segments. In some embodiments, the number of segments may be selected based on an input from a user. In other embodiments, the number of segments may be selected based on a default value or data file.

In some embodiments, the size and/or shape of one or more of the segments may be based on default values. At step 230, the size and/or shape of one or more segments may be modified to generate a unique head structure. In some embodiments, the size and/or shape of one or more segments may be modified based on an input from a user. In other embodiments, the size and/or shape of one or more segments may be modified pseudo-randomly. For example, the boundary of one or more segments may be adjusted within a predefined range, which may be selected based on a user input, based on a default value, based on a probability density function, or based on other selection criteria. A boundary of a segment may be modified by adding or removing cells adjacent to an initial boundary of the segment. For example, cells may be added to the segment such that the region of the head to which the segment corresponds is expanded by 2 mm.

When the boundary of one or more segments is expanded or contracted, one or more segments may overlap and/or gaps may appear between adjacent segments. In some embodiments, where one or more segments overlap, the boundary of each overlapping segment may be withdrawn by equal amounts to eliminate the overlap. In other embodiments, where a gap appears adjacent to one or more segments, the boundary of each segment adjacent to the gap may be expanded by equal amounts to eliminate the gap.

At step 240, one or more pathologies may be inserted into the model. A pathology may correspond to any neuropathology, such as a tumor, cerebral microbleed, microhemorrhage, or other pathology. A pathology may have a unique size, shape, or other characteristics based on the type of pathology.

A pathology may be inserted into the model by adding a new segment to the model corresponding to the pathology. In some embodiments, the size, shape, type, and/or location of a pathology may be determined based on an input from a user. Alternatively, a pathology may be generated and inserted into the model pseudo-randomly. For example, a pathology type, size, shape, and/or location may be selected pseudo-randomly, and the pathology may be inserted into the model at the selected location. In some embodiments, the system may store information, such as a data file, that includes probability values correspond to pathology types, shapes, sizes, and/or locations, and pathologies may be generated and inserted based on the stored probabilities.

At step 250, the cells of the data array may be populated with tissue property values to generate a numerical model. In some embodiments, the cells may be populated using one or more probability distributions. A probability distribution may comprise one or more tissue property values and corresponding probability values associated with a tissue property. For each segment of the model, a tissue property value may be selected based on a probability distribution associated with the region. In some embodiments, a probability distribution may be associated with one tissue property for one segment of the head. For example, one probability distribution may comprise values corresponding to iron concentration in a first segment of the head, and a second probability distribution may store values corresponding to T2 values for a second segment of the head.

A probability distribution may be generated based on a sample of tissue property measurements associated with a segment of the head. A probability distribution may be a Gaussian distribution centered on an average tissue property value. Tissue property measurements may be based on clinical MRI scans, for example, on 3 T magnets. Tissue property measurements may also be obtained based on other methods, such as absorption spectrometry, plasma spectroscopy, mass spectroscopy, neutron activation analysis, particle-induced X-ray emissions, and/or other methods.

In some embodiments, a probability distribution may be stored as a data object, such as an array, table, list, tree, linked list, or other data structure suitable for storing related data values. A probability distribution may be created and/or stored in memory, such as storage 140 described with respect to FIG. 1, above.

Values corresponding to different tissue properties may be stored in different probability distributions. For example, a probability distribution may comprise values corresponding to one tissue property, such as iron concentration, electromagnetic tissue property, real oximetry, tissue molecular composition, T1, T2, T2*, or other magnetic resonance property.

More than one probability distribution may correspond to the same tissue property and segment, but each distribution may store data based on different subsets of patients. For example, a probability distribution may comprise values corresponding to a particular class of patients, such as men, women, adults, children, senior citizens, individuals with certain medical conditions, such as Parkinson's, Alzheimer's, individuals with certain pathologies, such as cerebral microbleeds, cerebral edema, or history of stroke, or other characteristics. By populating the array based on a distribution corresponding to a particular class of patients, the method may generate a numerical model that accurately models tissue properties corresponding to a particular population of interest.

In some embodiments, a probability distribution may comprise values corresponding to patients satisfying multiple criteria. For example, the data array created and/or stored in memory may be populated based on a probability distribution comprising values based on measured tissue properties of patients over the age of 65 and who have had a stroke. In this way, the method may generate a numerical model that accurately models tissue properties of a patient over the age of 65 who has had a stroke, rather than all patients over the age of 65 or all patients who have had a stroke. Similarly, a segment corresponding to an inserted pathology, such as a tumor or cerebral microbleed, may be populated based on one or more probability distributions that comprise values corresponding to the pathology.

At step 260, for each segment in the data array, a tissue property value may be selected based on a probability distribution corresponding to a tissue property, region, and/or type of patient of to be modeled. A tissue property value may be selected based on a selected probability distribution. By selecting tissue property values based on probability distributions, unique numerical models may be generated having unique tissue properties.

In some embodiments, each cell in the data array may be populated with only one value corresponding to one tissue property. In other embodiments, one or more cells in the data array may be populated with multiple values corresponding to multiple tissue properties based on different probability distributions. In this way, a single numerical model may model multiple tissue properties.

The data array may be populated based on different sets of probability distributions. For example, the data stored in a particular set of probability distributions may be based on a particular data source, such as a particular set of tissue samples, clinical trials, or other sources of tissue property values. Thus, different sets of probability distributions may correspond to different data sources. When the data array is populated, the tissue property values may be selected from a particular set of probability distributions corresponding to a particular data source. In some embodiments, the set of probability distributions used to populate the array may be selected based on a user specification.

In some embodiments, the data array created and/or stored in memory may be formatted to facilitate use of the numerical model. Formatting the data array may comprise adding header information to the array and/or adding header information to each cell in the array and/or storing the array as a particular type of output file. For example, the data array may be stored as a Comma Separated Value file (CSV), Excel file (XLS), or other file type suitable for storing a set of related data. In some embodiments, the data array may be formatted in accordance with the input requirements for particular MRI simulation software. In this way, the numerical model generated by the method may be directly used as an input to an MRI simulator. In other embodiments, the array may be formatted and stored according to a standard file format for medical imaging, such as DICOM or NIFTI. In this way, the numerical model generated by the method may be opened by imaging software and displayed as the output of a magnetic resonance scan.

Alternatively, the data array may be formatted to match the output format of a clinical MRI scan. In this way, the numerical model generated by the method may be directly compared to the output of a real MRI scan.

Figure 4:
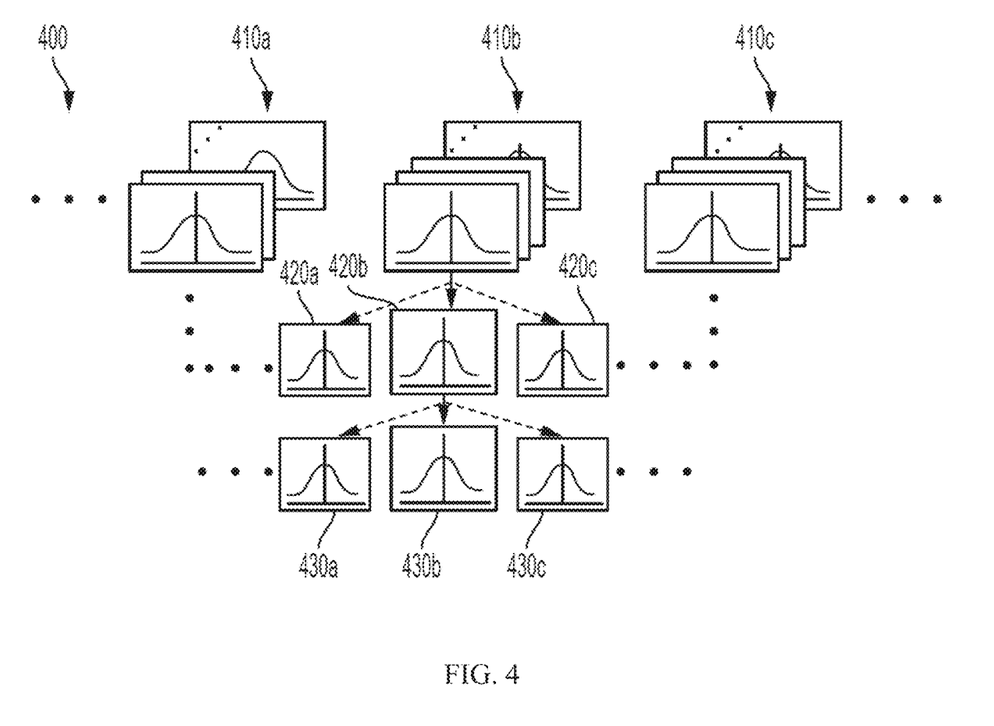
FIG. 4 is a visual representation of a library of tissue property probability distributions, according to some embodiments.

FIG. 4 shows a visual representation of a library of probability distributions, according to some embodiments. The library 400 may comprise one or more sets 410a-410c of probability distributions. Each set of lookup tables may comprise tissue property values obtained from different sources. For example, data composing each set of probability distributions may be derived from a different set of tissue samples, clinical trials, or other source of tissue property values.

Each set of probability distributions may comprise one or more sets of tissue property distributions 420a-420c. Each set of tissue property distributions may comprise tissue property probability distributions corresponding to a particular tissue property, such as iron concentration, and segment of the head. For each tissue property, one or more sub-distributions 430a-430c may be stored that comprise tissue property probability distributions that correspond to a segment of the head. For each segment of the head, one or more distributions may be stored corresponding to particular groups of patients, such as men, women, adults, children, senior citizens, individuals with certain medical conditions, such as Parkinson's, Alzheimer's, individuals with certain pathologies, such as cerebral microbleeds, cerebral edema, or history of stroke, or other characteristics.

In some embodiments, a tissue property probability distribution may comprise a distribution that includes tissue property values corresponding to an entire population of patients—that is, all persons for which data corresponding to the particular tissue property is available. The tissue property distribution may also include one or more sub-distributions corresponding to a sub-population.

Figure 5:
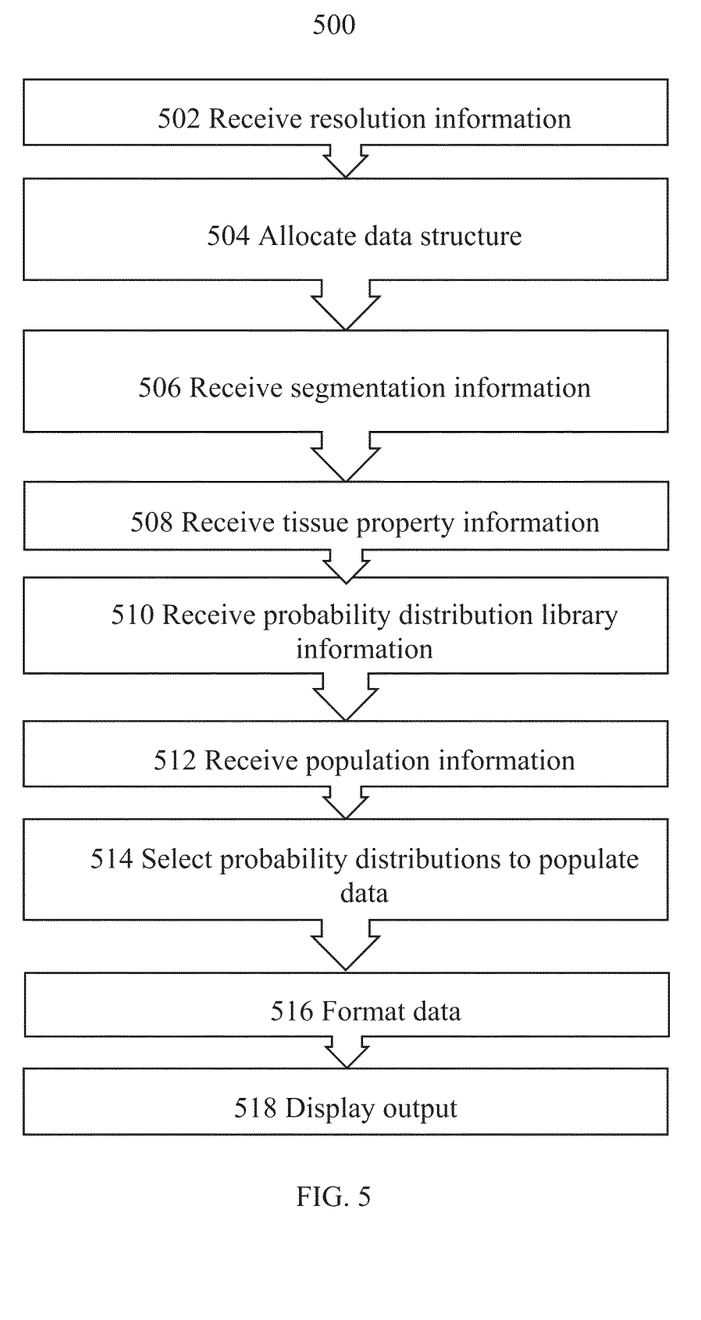
FIG. 5 is a flow diagram that illustrates a process for configuring an application to generate a numerical model of a human head, according to some embodiments.

FIG. 5 illustrates a method 500 for configuring a magnetic resonance modeling system to generate a numerical model of the human head, according to some embodiments. In some embodiments, method 500 may be performed at a system such as system 100 discussed above with reference to FIG. 1. In some embodiments, method 500 may enable a user to configure and generate a numerical model of the human head, including configuring the size and/or resolution of the model, the tissue properties incorporated in the model, and the output format of the model.

At step 502, a system may receive an input corresponding to a size and/or resolution of a numerical model to be created. In some embodiments, the system may display a prompt, such as a text field, drop-down menu, or other input field, asking a user to enter or select a size and/or resolution value. The input may correspond to a number of pixels, voxels, cells, data structures, or any other quantity that defines the number of data values comprising the numerical model to be generated.

At step 504, the system may allocate a data structure corresponding to the size information received at step 502. The system may allocate a data structure in memory, such as storage 140 described with respect to FIG. 1, above. The system may allocate storage space in the form of an array, a table, a list, a tree, a linked list, or any other data structure suitable for storing related data. In some embodiments, storage space may be allocated in advance. Alternatively, storage space may be allocated dynamically as each data value composing the numerical model is selected and stored.

At step 506, the system may receive information identifying segments of the numerical model that should be grouped together. For example, the system may receive information indicating that cells corresponding to the frontal cortex should be grouped together. In some embodiments, the system may display a prompt, such as a text field, drop-down menu, check-boxes, radio buttons, or other input field, asking a user to select from a predefined list of segmentations. In other embodiments, the system may display an image-based interface allowing a user to define segments of the numerical model. In some embodiments, the system may allow a user to only select segmentations for which tissue property probability distributions are available.

At step 508, the system may receive information corresponding to one or more tissue properties to be modeled by the numerical model. In some embodiments, the system may display a prompt, such as a text field, drop-down menu, check-boxes, radio buttons, or other input field, asking a user to enter or select one or more tissue properties to be modeled by the numerical model. In some embodiments, the system may be configured to select a default property if one is not selected by a user.

At step 510, the system may receive information corresponding to a library of probability distributions to be used to generate the numerical model. In some embodiments, the system may display a prompt, such as a text field, drop-down menu, check-boxes, radio buttons, or other input field, asking a user to enter or select a library of probability distributions to be used to generate the numerical model. In some embodiments, the prompt may be dynamically generated based on prior selections made by the user. For example, if a user has specified a particular tissue property to be modeled, the prompt may only display libraries that contain values corresponding to the selected tissue property. In some embodiments, the system may be configured to select a default library if one is not selected by a user.

At step 512, the system may receive information indicating for which population of patients probability distributions should be selected. In some embodiments, the system may display a prompt, such as a text field, drop-down menu, check-boxes, radio buttons, or other input field, asking a user to enter or select a population value to for which to generate the numerical model. For example, a user may select all patients or some subgroup of patients on which the tissue property values should be selected, such as children, seniors, or other criteria. In some embodiments, the user may select multiple population parameters. For example, a user may specify that a model should be based on data corresponding to individuals over the age of 65 and corresponding to individuals who have had a stroke. In some embodiments, the prompt may be dynamically generated based on prior selections made by the user.

At step 514, the system may access the library of probability distributions to populate the data array, such as according to steps 250-270, above. As above, the system may select a library based on an input from a user or based on a default configuration. For each segment and tissue property, the system may select a probability from the selected library that corresponds to the patient population to be modeled. Based on the selected tissue property probability distribution, a tissue property may be selected based the selected tissue property probability distribution, and the selected tissue property value may be stored in the corresponding cells in the array corresponding to the segment.

At step 516, the system may format the data array. In some embodiments, the system may format the data array in accordance with one or more inputs received from a user. For example, a user may specify that the data array be formatted to meet the input requirements of a particular MRI simulator or medical imaging software. Alternatively, the system may be configured to format the data array in accordance with a default selection in the absence of a selection from a user.

At step 518, the system may display the model generated by the method. For example, if the output is formatted to correspond to an output of a clinical or simulated MRI scan, the system may display the generated numerical model as the output of a simulated or clinical MRI scan. Alternatively, the system may display the generated numerical model based on a standard medical imaging format and/or software.

In other embodiments, the order of the steps of method 500 may vary. For example, a system may prompt a user to select a library of lookup tables before selecting tissue properties to be modeled. For any order, the system may dynamically populate prompts or input fields for later inputs based on earlier selections made by the user.

Numerical models, such as generated by method 200 above, may be used in many applications. For example, a numerical model may be used to validate an MRI measurement method based on a numerical model. A numerical model may be used to determine whether a measurement method accurately measures a tissue property and/or accurately detects a neuropathology. Additionally, a numerical model may be used to determine the accuracy limits of a measurement method, such as exam time, resolution, or other characteristics.

Figure 6:
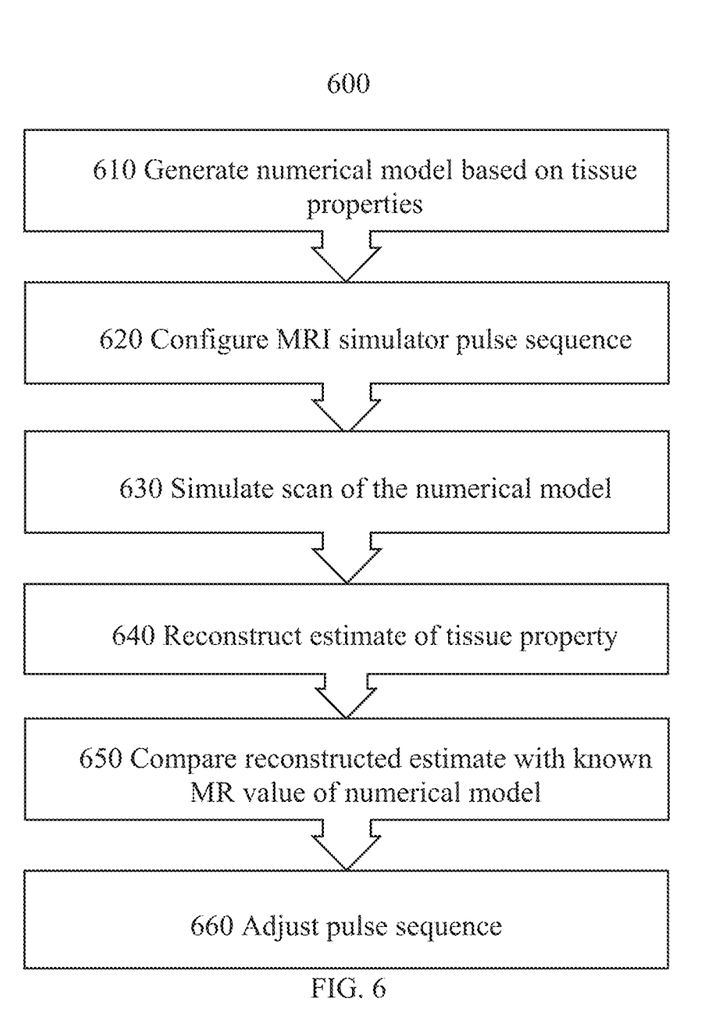
FIG. 6 is a flow diagram that illustrates a process for testing MRI pulse sequences, according to some embodiments.

A numerical model may also be used to validate and/or optimize new MRI measurement methods, such as pulse sequences. FIG. 6 illustrates a method 600 for validating and/or optimizing an MRI pulse sequence based on a numerical model, according to some embodiments.

At step 610, a numerical model may be generated, such as by method 200 above. The numerical model may be based on a particular tissue property, such as oxygenation, EMTP susceptibility, real oximetry, or other tissue property. The numerical model may be stored in a format that can be used as an input to an MRI simulator.

At step 620, an MRI simulator may be configured to simulate an MRI scan of the numerical model based on a first pulse sequence, such as by setting pulse sequence parameters such as TE, TR, BW, flip angle, sampling strategy, voxel size, FOV, and/or other parameters.

At step 630, the MRI simulator may perform a simulated scan using the numerical model as input to generate a simulated magnetic resonance image based on the tissue property values incorporated in the numerical model and the simulated pulse sequence. At step 640, based on the output of the simulated MRI scan, an estimate of the tissue property incorporated in the numerical model may be reconstructed based on the simulated MRI method. For example, an estimate of the tissue property incorporated in the numerical model may be reconstructed based on the simulated pulse sequence and post processing. At step 650, the reconstructed estimate may be compared to the known tissue properties of the numerical model.

At step 660, based on differences between the reconstructed estimate of the tissue property and the known tissue properties of the numerical model, the pulse sequence may be adjusted such that the output of the MRI scan may be used to more accurately reconstruct the known magnetic resonance properties of the numerical model. For example, one or more pulse sequence parameters, such as TE, TR, BW, flip angle, sampling strategy, voxel size, FOV, and/or other parameters, may be adjusted based on the difference between the simulated scan and the known magnetic resonance values. In this way, a numerical model, such as generated according to method 200, may be used to optimize pulse sequences of clinical MRI scans to more accurately measure magnetic resonance properties.

Additionally, one or more numerical models, such as generated according to method 200 above, may be used to train a machine learning classifier to analyze MRI scans. For example, certain pathologies, such as cerebral microbleeds, are difficult to detect in MRI scans by the human eye. However, a machine learning classifier may be trained using numerical models to detect microbleeds in MRI scans that would otherwise be difficult to detect or undetectable by human analysis.

Figure 7:
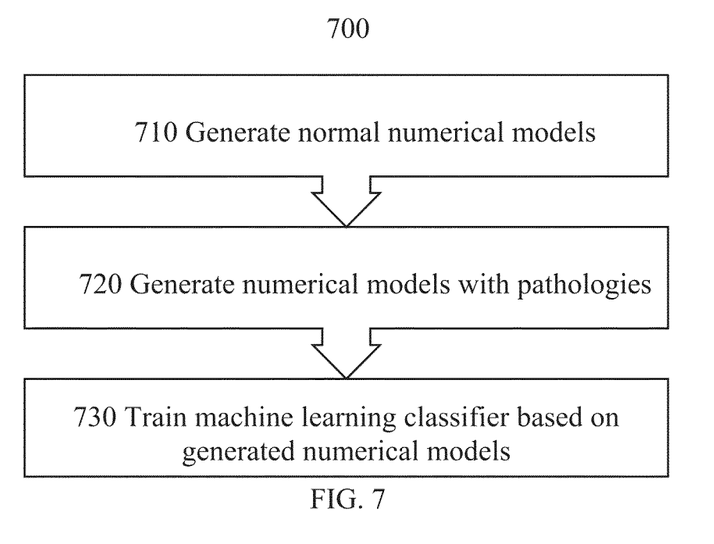
FIG. 7 is a flow diagram that illustrates a process for training a machine learning algorithm to detect neuropathologies, according to some embodiments.

FIG. 7 illustrates a method 700 for training a machine learning classifier to detect pathologies, such as cerebral microbleeds, tumors, or strokes, in MRI scans.

At step 710, one or more normal numerical models may be generated, such as by method 200 above, based on one or more tissue properties, such as EMTP susceptibility. To enable comparison of the training data with MRI scans, the numerical models may be formatted according to a medical imaging standard, such as described at step 220 of method 200 above. At step 720, a plurality of numerical models may be generated that include one or more pathologies having different characteristics. For example, to train a machine learning classifier to detect cerebral microbleeds, a plurality of numerical models may be generated that comprise a cerebral microbleed. The microbleeds may be inserted into the numerical models, such as described in step 220 of method 200 above, in different locations of the numerical models. Additionally, the inserted cerebral microbleeds may be generated with different characteristics. For example, the inserted cerebral microbleeds may have different sizes, shapes, orientations, or other characteristics.

At step 730, numerical models generated at steps 710 and 720 may be used as training data for a machine learning classifier to generate rules for determining whether an MRI scan contains a pathology and for identifying characteristics of the pathology.

The foregoing description sets forth exemplary methods, parameters and the like. It should be recognized, however, that such description is not intended as a limitation on the scope of the present disclosure but is instead provided as a description of exemplary embodiments. The illustrative embodiments described above are not intended to be exhaustive or to limit the disclosure to the precise forms disclosed. Many modifications and variations are possible in view of the above teachings. The embodiments were chosen and described to best explain the principles of the disclosed techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. In the foregoing description of the disclosure and embodiments, reference is made to the accompanying drawings, in which are shown, by way of illustration, specific embodiments that can be practiced. It is to be understood that other embodiments and examples can be practiced, and changes can be made without departing from the scope of the present disclosure.

Although the foregoing description uses terms first, second, etc. to describe various elements, these elements should not be limited by the terms. These terms are only used to distinguish one element from another. In addition, it is also to be understood that the singular forms "a," "an," and "the" used in the foregoing description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The present disclosure also relates to a device for performing the operations herein. This device may be specially constructed for the required purposes, or it may include a general purpose computer selectively activated or reconfigured by a computer program stored in the computer. Such a computer program may be stored in a non-transitory, computer readable storage medium, such as, but not limited to, any type of disk, including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referenced in this disclosure may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present disclosure is not described with reference to any particular programming language. It will be appreciated that a variety of programming languages may be used to implement the teachings of the present disclosure as described herein.

The invention claimed is:

1. A method for generating a numerical model of a human head, comprising:
   generating an array in a memory of a magnetic resonance modeling system, each cell in the array corresponding to a location in the head, wherein generating the array comprises:
      grouping cells of the array that correspond to different segments of the head, wherein a number of cells belonging to a group is based on one or more characteristics of the segment of the head associated with the grouped cells; and
      populating the grouped cells of the array to generate a numerical model using one or more probability distributions of tissue property values of a head, wherein the probability distributions comprise tissue property values associated with locations in the head and corresponding probability values, and wherein populating the grouped cells comprises:
         for each group of cells, determining a tissue property value based on one or more probability distributions associated with the segment of the head to which the group of cells corresponds.

2. The method of claim 1, comprising inputting the numerical model into an MRI simulator to generate a simulated magnetic resonance image based on a simulated pulse sequence.

3. The method of claim 2, comprising reconstructing an estimate of the tissue property values selected from the one or more probability distributions based on the simulated pulse sequence.

4. The method of claim 3, comprising comparing the reconstructed estimate of the tissue property values to the tissue property values on which the numerical model is based.

5. The method of claim 4, comprising adjusting the simulated MRI pulse sequence based on differences between the reconstructed estimate of the tissue property values and the tissue property values on which the numerical model is based.

6. The method of claim 2, comprising:
   comparing the simulated magnetic resonance image with an output of a clinical MRI machine; and
   calibrating the clinical MRI machine based on differences between the simulated magnetic resonance image and the output of the clinical MRI machine.

7. The method of claim 1, wherein populating the grouped cells of the array further comprises inputting the determined tissue property value into the corresponding cells.

8. The method of claim 1, wherein the probability distributions comprise Gaussian distributions based on one or more measurements of tissue property values.

9. The method of claim 1, wherein populating the grouped cells of the array using one or more probability distributions of tissue property values of a head comprises selecting, for each group of cells, a probability distribution corresponding to a tissue property.

10. The method of claim 1, wherein the tissue property value is randomly selected based on the one or more probability distributions.

11. The method of claim 1, wherein at least one group of cells corresponds to a neuropathology.

12. The method of claim 1, wherein populating the grouped cells of the array further comprises selecting a probability distribution from a plurality of libraries of probability distributions, each library of probability distributions comprising tissue property values derived from a different measurements.

13. The method of claim 1, wherein the probability distributions comprise tissue property values corresponding to a tissue property selected from the group consisting of electromagnetic tissue property susceptibility, iron concentration, real oximetry, tissue molecular composition, T1, T2, or T2*.

14. The method of claim 1, wherein the magnetic resonance modeling system is an MRI simulator.

15. The method of claim 1, wherein the cells composing the one or more groups of cells correspond to adjacent locations in the head.

16. The method of claim 15, comprising adjusting a boundary of at least one of the one or more groups of cells by adding or removing at least one cell.

17. A electronic system comprising:
one or more processors;
one or more memories; and
one or more programs, wherein the one or more programs are stored in the one or more memories and configured to be executed by the one or more processors, the one or more programs including instructions for:
generating an array in the one or more memories, each cell in the array corresponding to a location in a head, wherein generating the array comprises:
grouping cells of the array that correspond to different segments of the head, wherein a number of cells belonging to a group is based on one or more characteristics of the segment of the head associated with the grouped cells; and
populating the grouped cells of the array to generate a numerical model using one or more probability distributions of tissue property values of a head, wherein the probability distributions comprise tissue property values associated with locations in the head and corresponding probability values, and wherein populating the grouped cells comprises:
for each group of cells, determining a tissue property value based on one or more probability distributions associated with the segment of the head to which the group of cells corresponds.

18. A non-transitory computer-readable storage medium storing instructions for generating a numerical model of a human head, the instructions configured to be executed by one or more processors of a system comprising a display, and one or more processors, the instructions configured to cause the system to:
generate an array in a memory of a magnetic resonance modeling system, each cell in the array corresponding to a location in the head, wherein generating the array comprises:
grouping cells of the array that correspond to different segments of the head, wherein a number of cells belonging to a group is based on one or more characteristics of the segment of the head associated with the grouped cells; and
populating the grouped cells of the array to generate a numerical model using one or more probability distributions of tissue property values of a head, wherein the probability distributions comprise tissue property values associated with locations in the head and corresponding probability values, and wherein populating the grouped cells comprises:
for each group of cells, determining a tissue property value based on one or more probability distributions associated with the segment of the head to which the group of cells corresponds.

* * * * *